(12) United States Patent
Ben-Ezra (10) Patent No.: US 8,725,508 B2
(45) Date of Patent: May 13, 2014

(54) METHOD AND APPARATUS FOR ELEMENT IDENTIFICATION IN A SIGNAL

(75) Inventor: Yossef Ben-Ezra, Rehovot (IL)

(73) Assignee: Novospeech, Petach Tikva (IL)

( * ) Notice: Subject to any disclaimer, the term of this patent is extended or adjusted under 35 U.S.C. 154(b) by 126 days.

(21) Appl. No.: 13/431,270

(22) Filed: Mar. 27, 2012

(65) Prior Publication Data
US 2013/0262116 A1  Oct. 3, 2013

(51) Int. Cl.
*G10L 15/04* (2013.01)

(52) U.S. Cl.
USPC ............ 704/254; 704/214; 704/219; 704/226; 704/229; 704/233; 704/246; 704/249; 704/255; 704/256.4; 704/501; 84/654

(58) Field of Classification Search
USPC ......... 704/254, 214, 219, 226, 229, 233, 246, 704/249, 255, 256.4, 501; 84/654
See application file for complete search history.

(56) References Cited

U.S. PATENT DOCUMENTS

| | | | |
|---|---|---|---|
| 5,737,485 A | 4/1998 | Flanagan et al. | |
| 5,812,970 A * | 9/1998 | Chan et al. | 704/226 |
| 6,219,645 B1 | 4/2001 | Byers | |
| 6,224,636 B1 * | 5/2001 | Wegmann et al. | 704/246 |
| 6,226,608 B1 * | 5/2001 | Fielder et al. | 704/229 |
| 6,937,980 B2 | 8/2005 | Kransy et al. | |
| 6,982,377 B2 * | 1/2006 | Sakurai et al. | 84/654 |
| 7,054,814 B2 * | 5/2006 | Okutani et al. | 704/256.4 |
| 8,041,578 B2 * | 10/2011 | Schnell et al. | 704/501 |
| 8,069,044 B1 * | 11/2011 | Moorer | 704/254 |
| 2003/0069727 A1 | 4/2003 | Kransy et al. | |
| 2003/0078770 A1 * | 4/2003 | Fischer et al. | 704/214 |
| 2005/0137730 A1 * | 6/2005 | Trautmann et al. | 700/94 |
| 2005/0261896 A1 * | 11/2005 | Schuijers et al. | 704/219 |
| 2009/0055170 A1 * | 2/2009 | Nagahama | 704/226 |
| 2009/0150146 A1 * | 6/2009 | Cho et al. | 704/233 |
| 2009/0150151 A1 * | 6/2009 | Sakuraba et al. | 704/246 |
| 2010/0211391 A1 * | 8/2010 | Chen | 704/249 |
| 2010/0305948 A1 * | 12/2010 | Simone et al. | 704/255 |
| 2011/0208517 A1 * | 8/2011 | Zopf | 704/211 |
| 2011/0282663 A1 * | 11/2011 | Talwar et al. | 704/233 |
| 2012/0114134 A1 * | 5/2012 | Li et al. | 381/77 |
| 2012/0185247 A1 * | 7/2012 | Tzirkel-Hancock et al. | 704/233 |

OTHER PUBLICATIONS

Erich Zwyssig et al., A Digital Microphone Array for Distant Speech Recognition, Proc. IEEE ICASSP—10, 2010.
Michael L. Seltzer, Microphone Array Processing for Robust Speech Recognition, Doctoral Dissertation, Carnegie Mellon University Pittsburgh, PA, USA 2003.

(Continued)

*Primary Examiner* — Michael Colucci
(74) *Attorney, Agent, or Firm* — The Law Office of Michael E. Kondoudis (57) ABSTRACT

A computer-implemented method and apparatus for searching for an element sequence, the method comprising: receiving a signal; determining an initial segment of the signal; inputting the initial segment into an element extraction engine to obtain a first element sequence; determining one or more second segments, each of the second segments at least partially overlapping with the initial segment; inputting the second segments into the element extraction engine to obtain at least one second element sequence; and searching for an element subsequence common to at least a predetermined number of sequences of the first element sequence and the second element sequences.

16 Claims, 5 Drawing Sheets

(56) References Cited

OTHER PUBLICATIONS

Michael L. Seltzer et al., Speech Recognizer-Based Microphone Array Processing for Robust Hands-Free Speech Recognition, Acoustics, Speech, and Signal Processing (ICASSP), 2002 IEEE International Conference on, May 2002.

E. Lleida, Robust Continuous Speech Recognition System Based on a Microphone Array, Acoustics, Speech and Signal Processing, 1998. Proceedings of the 1998 IEEE International Conference on, May 1998.

Yamamoto S. et al. Enhanced Robot Speech Recognition Based on Microphone Array Source Separation and Missing Feature Theory, Robotics and Automation, 2005. ICRA 2005. Proceedings of the 2005 IEEE International Conference on, Apr. 2005.

* cited by examiner

METHOD AND APPARATUS FOR ELEMENT IDENTIFICATION IN A SIGNAL

TECHNICAL FIELD

The present disclosure relates to signal processing in general, and to a method and apparatus for element identification in signals, in particular.

BACKGROUND

Audio processing generally refers to enhancing or analyzing audio signals for all kinds of purposes, such as improving audio quality, removing noise or echo, providing full duplex communication systems, improving results of audio analysis engines and tools such as continuous speech recognition, word spotting, emotion analysis, speaker recognition or verification, and others. On a higher level, improving the results of such audio analysis engines and tools, and optionally using further tools such as text analysis tools to process the resulting text, may assist in retrieving information associated with or embedded within captured or recorded audio signals. Such information may prove useful in achieving many personal or business purposes, such as trend analysis, competition analysis, quality assurance, improving service, root cause analysis of problems conveyed over voce interactions, or others.

Many audio signals to be processed comprise one or more speakers who may at times talk simultaneously, and may include, in addition to the speakers, also music, tones, background noise on either side of the interaction, or the like. Audio analysis performance, as measured in terms of accuracy, detection, real-time efficiency and resource efficiency, depends heavily on the quality and integrity of the input audio signals, on the available computing resources and on the capabilities of the computer programs that constitute the audio analysis process.

Many of the analysis tasks are highly sensitive to the audio quality of the processed interactions. Multiple speakers, as well as music which is often present on hold periods, tones, background noises such as street noise, ambient noise, convolutional noises such as channel type and handset type, keystrokes and the like, severely degrade the performance of these engines, sometimes to the degree of complete uselessness.

One of the most required yet challenging audio analysis applications is continuous speech recognition. Currently known speech recognition systems achieve reasonable performance in a noise-free environment in which speech segments are easily recognized. Noise free signal can be obtained, for example, by using a close-talking microphone worn near the mouth of the speaker.

Speech recognition systems may comprise as a first stage a phoneme recognition engine, and in particular classification engines such as a Gaussian Mixture Model (GMM) or a Hidden Markov Model (HMM) for extracting phonemes out of an audio signal, wherein the engine outputs the most probable phoneme sequence for an input audio signal, or others. Such classification engines operate under the assumption that the speech signal can be viewed as a piecewise stationary signal or a short-time stationary signal. Therefore, although the engines can generally report if the segment is silent and does not contain audio, still the engines are not designed to indicate that the signal contains noise rather than speech, and will not avoid outputting phonemes. However, noise is generally not a stationary signal. Therefore, when noise is input into a classification engines, the classification engine still outputs a phoneme sequence, although it is a rather random or incidental sequence, which degrades the overall recognition quality.

Some known solutions for providing signals with low Signal-to-Noise Ratio (SNR) include the usage of multiple microphones to capture the speech signal. Array-signal-processing techniques have been developed to combine multiple signals as captured by an array of microphones, to achieve high quality results. Microphone array-based speech recognition may be performed in two independent stages: processing the captured waveforms, followed by passing the optionally-combined and improved output waveform to the speech recognition system.

However, not all audio required for processing purposes can be captured or recorded in noise-free environments. For example, it is often impractical pr inconvenient for a speaker to wear a close-talking microphone, and as the distance between the speaker and the microphone increases, the speech signal may become increasingly susceptible to background noise and reverberation effects that significantly degrade speech recognition accuracy. This is especially problematic in situations where the locations of the microphones or the users are dictated by physical constraints of the environment, as in meetings, automobiles, on the street, or the like. In such situations, it is impractical to provide and use a plurality of microphones, and only a single input audio signal is available.

There is thus a need for a method and apparatus that enable obtaining improved results from an identification engine such as a phoneme identification engine, even for signals with low SNR.

BRIEF SUMMARY

One exemplary embodiment of the disclosed subject matter is a computer-implemented method performed by a computerized device, comprising: receiving a signal; determining an initial segment of the signal; inputting the initial segment into an element extraction engine to obtain a first element sequence; determining one or more second segments, the second segments at least partially overlapping with the initial segment; inputting the second segments into the element extraction engine to obtain one or more second element sequences; and searching for an element subsequence common to at least a predetermined number of sequences of the first element sequence and the second element sequences. The method can further comprise outputting the element subsequence, subject to finding the element subsequence. The method can further comprise repeating the steps of determining the second segments, inputting the second segments into the element extraction engine, and searching for the element subsequence. The method can further comprise repeating the steps of determining the second segments, inputting the second segments into the element extraction engine, and searching for the element subsequence, subject to not finding the element subsequence. The method can further comprise determining whether a stopping criterion has been met, and repeating the steps of determining the second segments, inputting the second segments into the element extraction engine, and searching for the element subsequence, only if the stopping criterion has not been met. Optionally, the stopping criterion is selected from the group consisting of: a predetermined number of segments has been selected and the initial segment is fully covered by the second segments. Optionally, the initial segment is determined using a method selected from the group consisting of: energy-based; autocorrelation; zero crossing; and arbitrary determination. Optionally, the element extraction engine is selected from the group consisting of: a Gaussian mixture model, an artificial neural network, a support vector machine, and a hidden Markov model. Optionally, the signal is selected from the group consisting of: an audio signal, a video signal, a motion signal, a seismic signal, ECG signal, and a bio-medical signal. Optionally, the element is a phoneme.

Another exemplary embodiment of the disclosed subject matter is an apparatus having a processing unit and a storage device, the apparatus comprising: a signal receiving component for receiving a signal; an initial segmentation component for determining an initial segment of the signal; an additional segment determination component for determining one or more second segments, the second segments at least partially overlapping with the initial segment; an element extraction engine for receiving the initial segment and the second segments, and providing a first element sequence and one or more second element sequences; and an element sequence matching component for searching for a element subsequence common to at least a predetermined number of sequences of the first element sequence and the second element sequences. Optionally, the element extraction engine is selected from the group consisting of: a Gaussian mixture model, an artificial neural network, a support vector machine, and a hidden Markov model. Optionally, the signal is selected from the group consisting of: an audio signal, a video signal, a motion signal, a seismic signal, ECG signal, and a bio-medical signal. Optionally, the element is a phoneme. The apparatus can further comprise a data and control flow management component.

Yet another exemplary embodiment of the disclosed subject matter is a computer program product comprising: a non-transitory computer readable medium; a first program instruction for receiving a signal; a second program instruction for determining an initial segment of the signal; a third program instruction for inputting the initial segment into an element extraction engine to obtain a first element sequence; a fourth program instruction for determining one or more second segments, the second segments at least partially overlapping with the initial segment; a fifth program instruction for inputting the second segments into the element extraction engine to obtain one or more second element sequences; and a sixth program instruction for searching for an element subsequence common to at least a predetermined number of sequences of the first element sequence and the second element sequences, wherein said first, second, third, fourth, fifth and sixth program instructions are stored on said non-transitory computer readable medium.

BRIEF DESCRIPTION OF THE SEVERAL VIEWS OF THE DRAWINGS

The present disclosed subject matter will be understood and appreciated more fully from the following detailed description taken in conjunction with the drawings in which corresponding or like numerals or characters indicate corresponding or like components. Unless indicated otherwise, the drawings provide exemplary embodiments or aspects of the disclosure and do not limit the scope of the disclosure. In the drawings.

DETAILED DESCRIPTION

The disclosed subject matter is described below with reference to flowchart illustrations and/or block diagrams of methods, apparatus (systems) and computer program products according to embodiments of the subject matter. It will be understood that blocks of the flowchart illustrations and/or block diagrams, and combinations of blocks in the flowchart illustrations and/or block diagrams, can be implemented by computer program instructions. These computer program instructions may be provided to one or more processors of a general purpose computer, special purpose computer, a tested processor, or other programmable data processing apparatus to produce a machine, such that the instructions, which execute via the processor of the computer or other programmable data processing apparatus, create means for implementing the functions/acts specified in the flowchart and/or block or blocks in the block diagram.

These computer program instructions may also be stored in a non-transient computer-readable medium that can direct a computer or other programmable data processing apparatus to function in a particular manner, such that the instructions stored in the non-transient computer-readable medium produce an article of manufacture including instruction means which implement the function/act specified in the flowchart and/or block diagram block or blocks.

The computer program instructions may also be loaded onto a device. A computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

One technical problem dealt with by the disclosed subject matter is the low quality of phoneme identification by classifier engines such as Gaussian Mixture Model (GMM), artificial neural network, Support Vector Machine (SVM), Hidden Markov Models (HMMs), or any other type of classifier or combination of classifiers operating on signals with low Signal-to-Noise Ratio (SNR). Many speech recognition techniques use classifiers for extracting phonemes out of an audio signal, wherein a classifier outputs the most probable phoneme sequence for the input audio signal. Classifiers operate under the assumption that the speech signal can be viewed as a piecewise stationary signal or short-time stationary signals. Classifiers can generally be trained to recognize particular types of signals as noises, wherein noise may be regarded as any part of the signal that is not related to the speech signal. However, a classifier can only be trained to recognize the types of noises it is trained upon and not any noise. Therefore, although the classifier can generally report if the segment is silent, contains noise it was trained upon, or does not contain audio, still the classifier is not designed to indicate that the signal is noisy for other types of noises, and will not avoid outputting phonemes. However, noise is generally not a stationary signal. Therefore, when a signal comprising arbitrary noise, with or without speech is input into a classifier, the classifier still outputs a phoneme sequence, although it is a rather random or incidental sequence, which may degrade the overall recognition quality.

For avoiding such situations, when processing an audio signal by a classifier such as an HMM, the signal first undergoes segmentation intended to separate the speech segments from the non-speech segments, so as to avoid processing non-speech segments by the classifier. However, when the signal has a low SNR, such segmentation is generally not very effective, resulting in low-quality output of the classifier.

The description below refers to HMM. However, it will be appreciated that HMM is merely an example and that the disclosure may also apply to any other classifier, such as GMM, SVM, or any other type of classifier or combination of classifiers.

One technical solution comprises utilizing the fact that noise is non-stationary, and thus the phonemes output by a classifier such as an HMM from a noise signal are quite random. In order to utilize this behavior, some initial segmentation is performed over the audio signal, for example by energy-based method, autocorrelation, zero crossing or other methods, to generate an initial segment. Then, one or more additional segments are created, which partially overlap with the initial segment. The initial segment and the additional segments are then processed by the classifiers. Since classifiers operating on noisy segments may output a random phoneme sequence, processing two such segments is unlikely to produce matching phoneme sequences for noisy parts. However, when a speech segment is processed twice, the classifier is likely to output the same phoneme sequence. Therefore, the phoneme sequences output by processing two or more partially overlapping segments are likely to converge on the speech segments, and are likely to diverge on the non-speech segments. In some embodiments, the process can start by analyzing two partially overlapping segments. If there is a phoneme sub-sequence which is common to the output phoneme sequences, then it is assumed that the audio associated with the sub-sequence indeed represents a speech segment. If there is no such common segment, then a third segment which partially overlaps with the first or the second segment may be processed, and common sub-sequences are searched between the third segment and any one or both of the first two segments. The process may continue until convergence is found between two or more phoneme sequences, such that the time window for which the common sub-sequence relates, is assumed to be a speech segment, and the classifier results are considered reliable. If no convergence is detected until a predetermined number of segments is processed, or until the full initial segment has been covered by other segments, or any other stopping criteria has been met, it is assumed that the segment contains just noise, or speech with unacceptable SNR, so that it should not be processed.

One technical effect of the disclosed subject matter relates to a method and apparatus for receiving more reliable phone sequences from a classification engine. For noisy input audio signals the method and apparatus will not output any phoneme sequences, thus avoiding erroneous sequences which degrade the overall classification performance.

Another technical effect of the disclosed subject matter relates to using multiple inputs to classification engine to obtain reliable results, but unlike microphone array solutions, all these inputs are derived from the same single audio signal, rather than from a multiplicity of audio signals. This usage of one input signal provides for the benefits of multiple inputs, without the price and technical burden of using a multiplicity of microphones.

Yet another technical effect of the disclosed subject matter relates to estimating the characteristics of the noisy channel. The additional segments are uncorrelated with the first segment due the random noisy signal. Therefore based on these un-correlated segments the noisy channel characteristics can be better estimated.

Figure 1A:
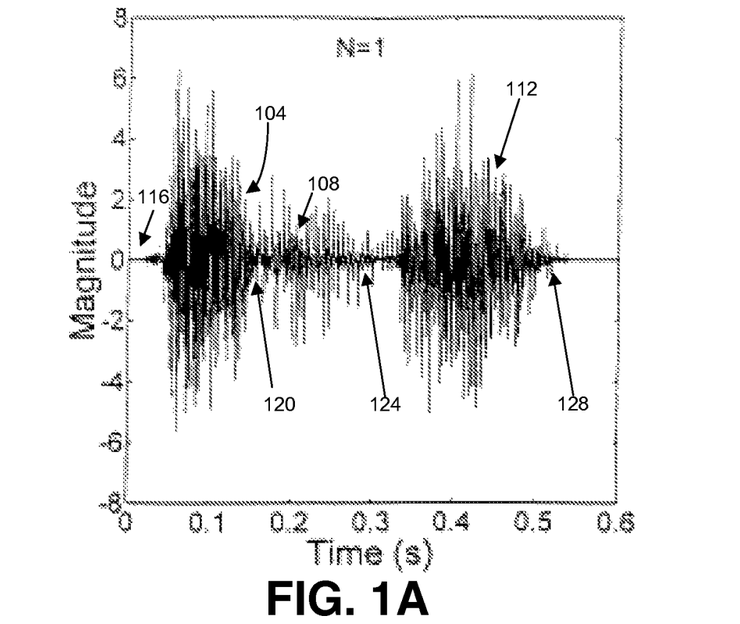
FIG. 1A shows a waveform of a signal with high signal-to-noise ratio.
Figure 1B:
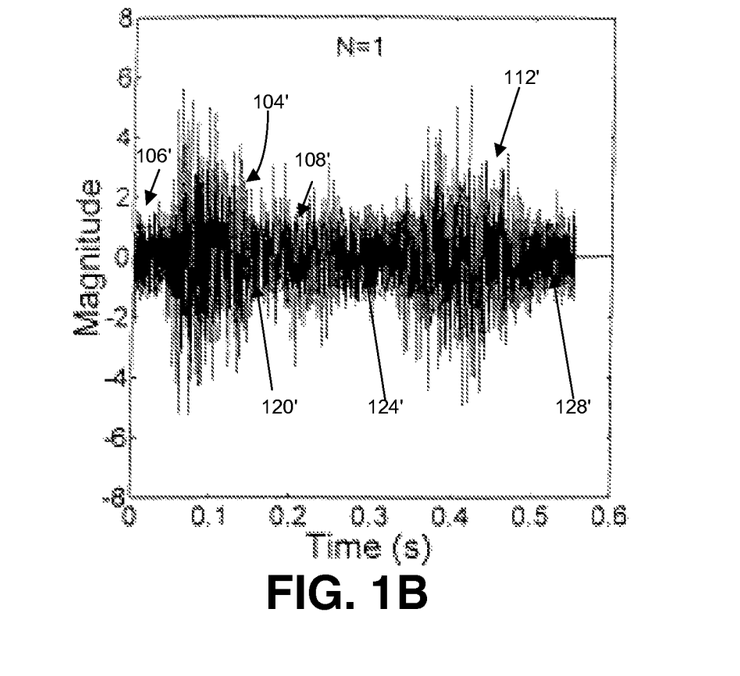
FIG. 1B shows a waveform of a signal with low signal-to-noise ratio.

Referring now to FIG. 1A and FIG. 1B showing, respectively, two audio signals of the same sound, wherein the waveform of FIG. 1A contains a relatively noise-free sound while the waveform of FIG. 1B is noisy.

It can be seen that when trying to segment the waveform, it is straight-forward to segment voiced areas 104, 108 and 112 of FIG. 1A from the surrounding areas referred to as areas 106, 120, 124 and 128. The segmentation can be performed, for example, by energy, autocorrelation, zero crossing or the like.

On the waveform of FIG. 1B, however, it is harder to segment the corresponding areas 104', 108' and 112' from the surrounding areas referred to as areas 106', 120', 124' and 128'. In particular, voice area 108' cannot be well segmented from areas 120' and 124'. Providing the waveform of FIG. 1B as input to an HMM will result in a phoneme sequence containing many incidental and wrong phonemes.

In some environments, the SNR of an audio signal to be processed may be more similar to the SNR of the waveform of FIG. 1B than to that of FIG. 1B, thus making segmentation a hard task, which results in poor HMM output.

Figure 2:
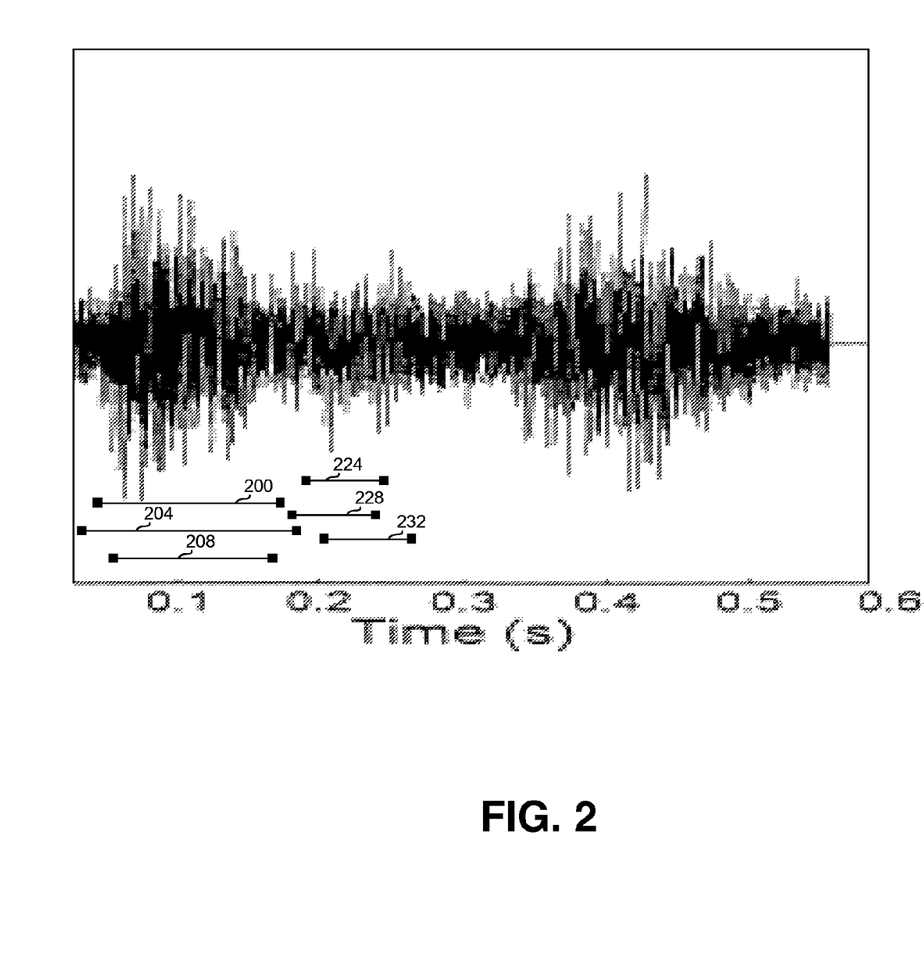
FIG. 2 shows a schematic illustration of temporally differing audio segments, in accordance with some exemplary embodiments of the disclosed subject matter.

Referring now to FIG. 2, showing schematic illustration of segmentation of an audio signal by using selecting temporally differing audio segments.

The waveform shown on FIG. 2 is the same as the waveform of FIG. 1B discussed above. On a first stage, some initial segmentation is performed using any known method such as energy-based, zero crossing, autocorrelation, or the like. Assume that the initial segmentation produces segment 200. Segment 200 is input into an HMM, and the output is a sequence of phonemes, <A B C D B C F>, wherein each letter represents a particular phoneme, and each phoneme may be associated with a time stamp or a time range. Then a slightly different segment is selected, such as segment 204, which starts about 0.01 second (10 mSec) before the start of segment 200, respectively and ends 0.01 second (10 mSec) after the end of segment 200. When inputting segment 204 into the HMM, the output is a sequence of phonemes <Q R G C D B E>. It can be seen that the phoneme sequence <C D B>, which occurs at substantially the same time window in both segments is common to both segments, an event which is unlikely to occur if the signal contained noise at that time window. A third segment can be examined as well, such as segment 208 which starts about 200 mSec after the start of segment 204 and ends about 200 mSec before the end of segment 204. Segment 208 may yield the <T C D B E R> sequence, wherein the time window of the <B C D> subsequence is in conformance with the time windows of the same subsequence of the sequences obtained from segments 200 and 204, which confirms the conclusion.

However, when selecting initial segment 220 and then segments 224 and 228, due to the high noise level no common sequence is identified, resulting in deducing that the area is noisy or does not contain speech. This decision, although causes "loss" of phoneme information, actually eliminates low quality and probably erroneous phoneme sequences, thus improving the overall recognition quality.

It will be appreciated that a constant pattern of segments can be selected: first the segment identified by the initial segmentation, followed by a segment that starts or ends a predetermined time before or after the initial segment, then another segment that starts or ends at another predetermined time before or after the initial segment or the second segment, and so on.

In some embodiments, two or more segments can be determined, followed by inputting the segments into the classification engines. Additionally or alternatively, one segment can be determined and then input to the classification engine, before or concurrently with determining a second segment.

Alternatively, the third and optionally further segments can be determined dynamically in accordance with the output of the classification engine for previous segments. For example, if the first and second segments provide a long common phoneme subsequence, the third segment can be selected to match the time window associated with the common subsequence in order to verify the phoneme subsequence. If, however, no common sequence is output for the first and second segments, the third segment can be selected to substantially extend one or both of the segments in order to locate a common subsequence with at least one of them.

The minimal length of the common phoneme subsequence or the associated time window which is required for deducing that the results are valid, can be predetermined, and can also depend on factors such as phoneme confidence or certainty, or other factors.

Figure 3A:
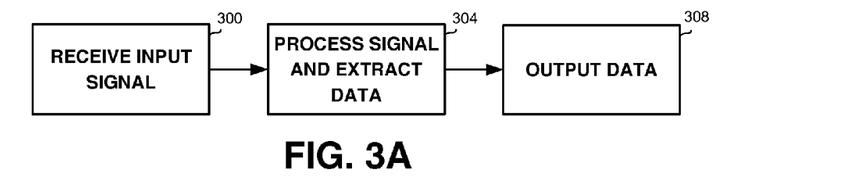
FIG. 3A is a schematic flowchart of steps in a method for receiving data from a signal, in accordance with some exemplary embodiments of the disclosed subject matter.

Referring now to FIG. 3A, showing a schematic flowchart of steps in a method for receiving data from a signal.

On step 300 a signal may be received. The signal may be any analog or digital signal, such as but not limited to an audio signal, a video signal, a motion signal, a seismic signal, a bio-medical signal such as ECG, or any other signal which may comprise noise.

On step 304 the input signal may undergo processing or data extraction. This step may comprise a multiplicity of substeps, for example the steps detailed in association with FIG. 3B below. In some embodiments, the signal may undergo some preprocessing intended for improving its quality, assessing the signal quality and discarding noisy parts, removing silent periods, or the like. Following the optional preprocessing, the signal may undergo processing, including for example speech recognition, emotion detection, keyword extraction, or the like.

On step 308, the data extracted on step 304 may be output in any required format, such as numeric, textual, binary, tabular data, or the like.

Figure 3B:
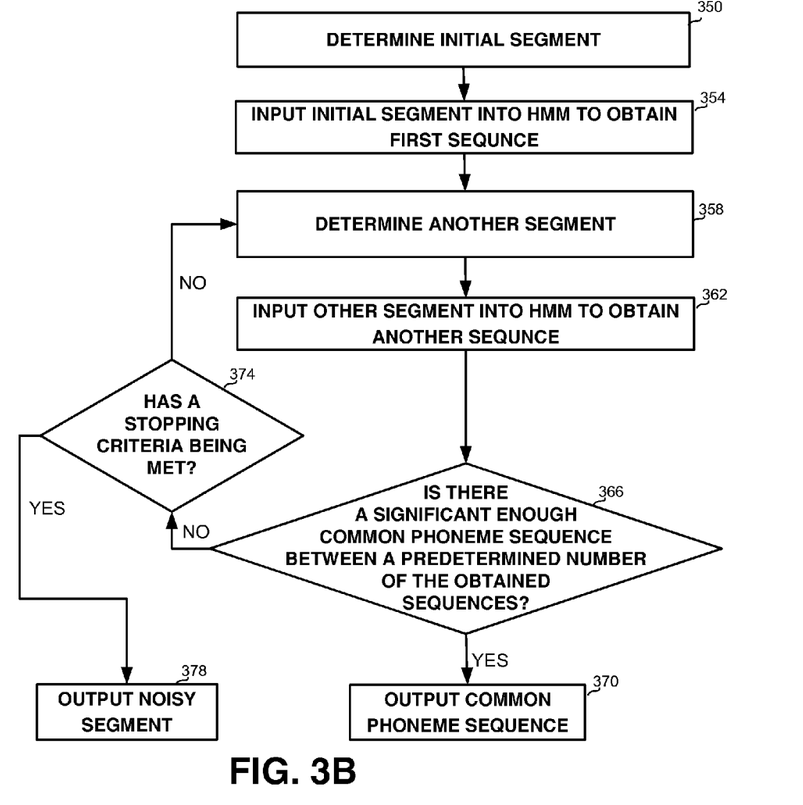
FIG. 3B is a flowchart of steps in a method for automatic audio segmentation, in accordance with some exemplary embodiments of the disclosed subject matter.

Referring now to FIG. 3B, showing a flowchart of steps in a method for improving the results of phoneme identification in an audio signal.

On step 350, an initial segment may be determined, for example by performing segmentation by any desired method such as energy-based, autocorrelation, zero crossing or even arbitrary segmentation.

On step 354 one of the initial segments is input into an HMM or another phoneme extraction engine, and a phoneme sequence is received.

On step 358 another segment may be determined, which partially overlaps with the initial segment or any other previously obtained segment. The second segment can be selected to start or end earlier or later than the initial segment, for example by a predetermined period of time.

On step 362 the segment selected on step 358 is input into the HMM or the other phoneme extraction engine, and another phoneme sequence is received.

On step 366 it may be determined if there exists a phoneme subsequence that is common to two or more of the received phoneme sequences, and that is significant enough. Significant enough may relate to the number of phonemes in the common subsequence, the probability of particular phonemes appearing in the common subsequence, or the like. The common subsequence may be found by exhaustive search, fuzzy search, or any other pattern matching technique. The common subsequence may also be verified using a linguistic model which may provide the probability or another indication for the phoneme sequence in the relevant language.

If there is such subsequence, on step 370 the common subsequence may be output. Outputting may refer to presenting to a user, storing in a volatile or persistent storage, passing to another engine, executable or other component for further processing, or the like.

It will be appreciated that if the common subsequence occurs on or close to the start or end of one or more of the segments, it may be attempted to extend the segment on that end prior to outputting, in order to make sure the segment is processed to its maximal length.

If there is no such subsequence, then on step 374 it is determined whether a stopping criteria has been met. A stopping criterion may relate to the number of segments that have been derived from the initial segment, the coverage of the initial segment by additional segments, or the like.

If such criteria has been met, then on step 378 it is output that the initial segment, or another segment which may contain or partially overlap with the initial segment is noisy, and no significant phoneme sequence can be retrieved.

If no such stopping criteria has been met, then execution goes back to step 308 and another segment is selected, which may overlap with one or more of the previously selected segments, and the process repeats for the new segment collection.

Figure 4:
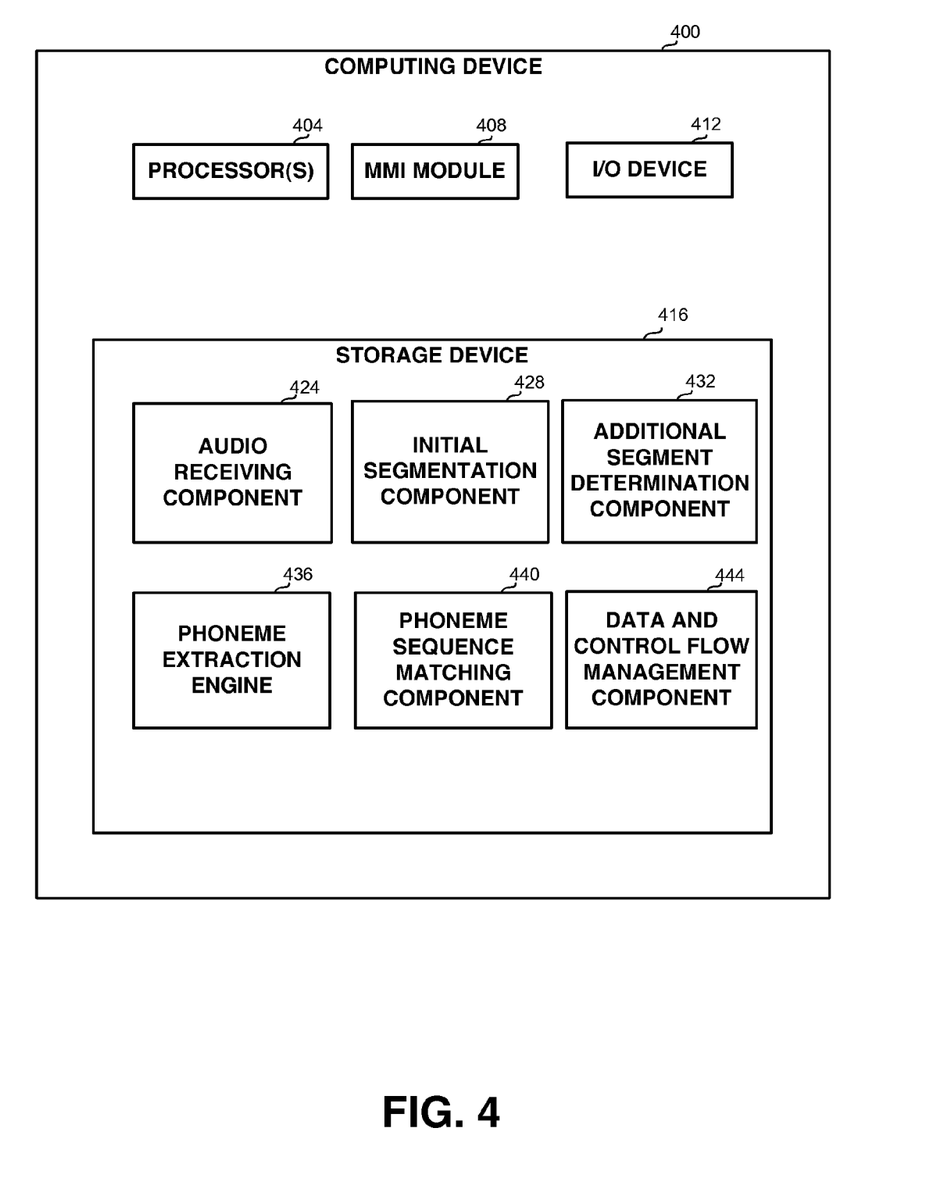
FIG. 4 shows a block diagram of components of an apparatus for automatic audio segmentation, in accordance with some exemplary embodiments of the disclosed subject matter.

Referring now to FIG. 4 showing a block diagram of components of an apparatus for improving the results of phoneme identification in an audio signal.

The apparatus comprises a computing device 400, which may comprise one or more processors 404. Any of processors 404 may be a Central Processing Unit (CPU), a microprocessor, an electronic circuit, an Integrated Circuit (IC) or the like. Alternatively, computing device 400 can be implemented as firmware written for or ported to a specific processor such as digital signal processor (DSP) or microcontrollers, or can be implemented as hardware or configurable hardware such as field programmable gate array (FPGA) or application specific integrated circuit (ASIC). Processors 404 may be utilized to perform computations required by computing device 400 or any of it subcomponents.

In some exemplary embodiments of the disclosed subject matter, computing device 400 may comprise MMI module 408. MMI module 408 may be utilized to provide communication between the apparatus and a user for providing input, receiving output or the like.

In some embodiments, computing device 400 may comprise an input-output (I/O) device 412 such as a terminal, a display, a keyboard, an input device or the like, used to interact with the system, to invoke the system and to receive results.

Computing device 400 may comprise one or more storage devices 416 for storing executable components, and which may also contain data during execution of one or more components. Storage device 416 may be persistent or volatile. For example, storage device 416 can be a Flash disk, a Random Access Memory (RAM), a memory chip, an optical storage device such as a CD, a DVD, or a laser disk; a magnetic storage device such as a tape, a hard disk, storage area network (SAN), a network attached storage (NAS), or others; a semiconductor storage device such as Flash device, memory stick, or the like. In some exemplary embodiments, storage device 416 may retain program code operative to cause any of processors 404 to perform acts associated with any of the steps shown in FIG. 3 above, for example receiving audio file, determining segments, determining common phoneme subsequences, or the like.

The components detailed below may be implemented as one or more sets of interrelated computer instructions, executed for example by any of processors 404 or by another processor. The components may be arranged as one or more executable files, dynamic libraries, static libraries, methods, functions, services, or the like, programmed in any programming language and under any computing environment. Storage device 416 may comprise or be loaded with one or more of the components, which can be executed on computing platform 400 by any one or more of processors 404. Alternatively, any of the executable components may be executed on any other computing device which may be in direct or indirect communication with computing platform 400.

Storage device 416 may comprise audio receiving component 424 for receiving audio signals. Audio signals can be received from any capturing device, from a storage device storing previously recorded or generated audio, from another computing device over a communication channel, or from any other source.

Storage device 416 may also comprise initial segmentation component 428 for segmenting an audio signal using any known method such as energy-based, autocorrelation, zero crossing, arbitrary selection or the like.

Yet another component loaded to storage device 416 may be additional segment determination component 432 for determining another segment containing or partially overlapping with any other one or more previously determined segments.

Storage device 416 may also comprise or be in association with one or more phoneme extraction engines 436 such as an HMM engine adapted to receive an audio segment and output a phoneme sequence it finds to be most probable.

Phoneme sequence matching component 440 which may also be loaded or stored on storage device 416 is adapted to receive two or more sequences of phonemes, in which phonemes may be associated with time stamps or time ranges, and search for common subsequences. The subsequences may be required to comply with one or more requirements, such as minimal length, significance of recognized phonemes, or the like. It will be appreciated that complete identity of the phonemes in the subsequence may not be required, e.g., if two sequences are similar in a long-enough subsequence, one or more phonemes of the subsequence may differ between the two sequences. The matching may be done using any required method such as exhaustive search, fuzzy search, or any other pattern matching technique.

Storage device 416 may also comprise data and control flow management component 444 for managing the flow of information and control between other components, for example passing an audio signal received by audio receiving component 424 to initial segmentation component 428, passing the output phoneme sequences to phoneme sequence matching component 440, or the like.

Figure 5:
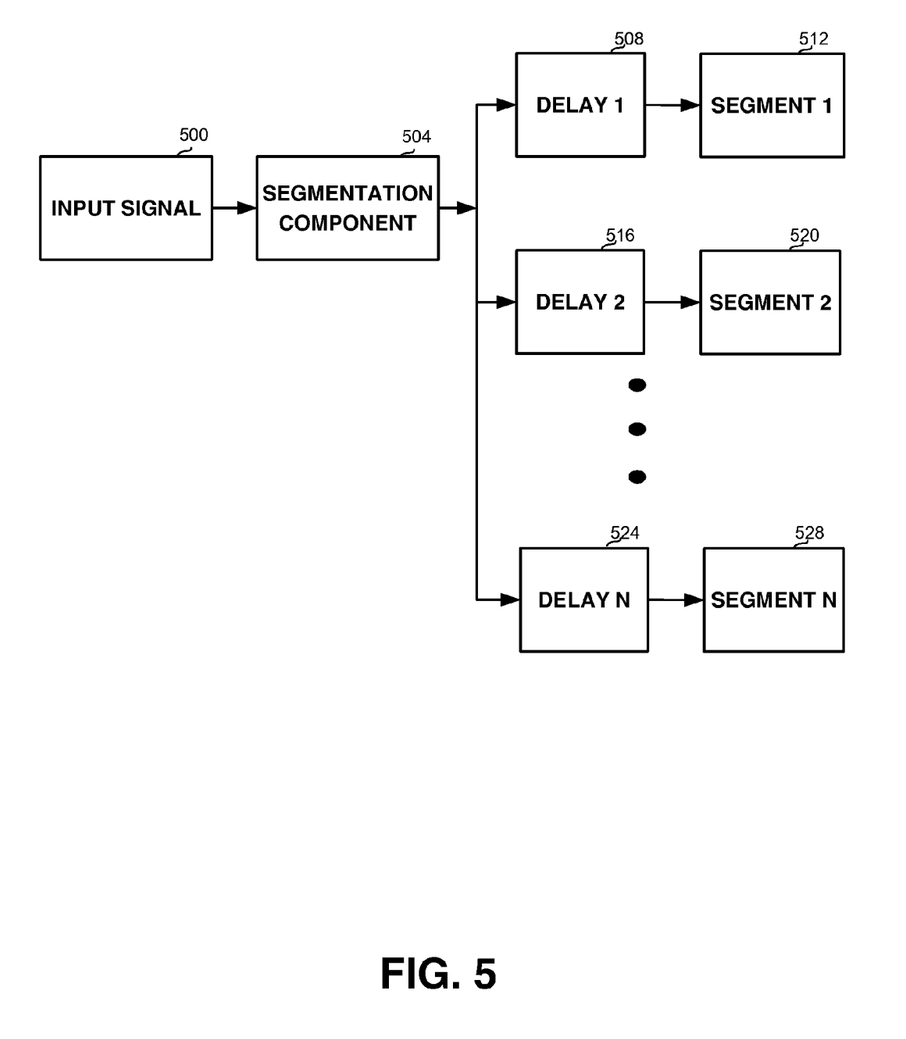
FIG. 5 is a schematic illustration of receiving time-shifted signals using delay lines, in accordance with some exemplary embodiments of the disclosed subject matter.

It will be appreciated that selecting time-shifted segments can alternatively be obtained by inputting a single audio signal into different delay lines. Thus, taking corresponding time windows from a multiplicity of delay lines fed with the same audio signal, will provide a multiplicity of time-shifted segments from the same input audio signal.

Referring now to FIG. 5, showing a schematic illustration of receiving time-shifted signals using delay lines, in accordance with some exemplary embodiments of the disclosed subject matter.

Input signal 500 is received from any source, such as a microphone, a recording device, or the like. Signal 500 may be input into a segmentation component 504 which indicates one or more specific segments of input signal 500. Segmentation component 504 may apply any initial segmentation algorithm, output segments of predetermined length, or the like. The one or more segments output by segmentation component 504 are input into delay component 1 (508) which outputs segment 1 (512), delay component 2 (516) which outputs segment 2 (520), and so on in accordance with the required or minimal number of segments, until delay component N (524) outputting segment N (528). It will be appreciated that in some embodiments segmentation component 504 can be omitted, and that each delay component such as delay component 1 (508), delay component 2 (516) or delay component N (524) may implement the segmentation. In other embodiments, input signal 500 may be received as a sequence of segments, which may also make segmentation component 504 redundant.

The disclosed method and apparatus provide for extracting enhanced results from a classifier operating on audio signals comprising noise which the classifier was not trained upon, and which is not related to the speech carried by the audio signal. Since time-shifted noisy audio signals provide different phoneme sequences for overlapping segments, ruling out non-corresponding phoneme sequences may be used for eliminating erroneous outputs from noisy segments.

It will be appreciated that the disclosed method and apparatus can be used, mutatis mutandis for other signals or purposes, such as video signals in which common features are to be searched for, bio-medical signals such as ECG taken in noisy conditions, signal form a motion sensor, seismic signal, signal received from a gyroscope, or any other signal. Wherein an audio signal may be searched for phonemes, other signals may be searched for other relevant building blocks or elements. Thus, the phoneme search engine may be any element extraction engine, and sequences of elements may be compared.

The flowchart and block diagrams in the figures illustrate the architecture, functionality, and operation of possible implementations of systems, methods and computer program products according to various embodiments of the present disclosure. In this regard, each block in the flowchart and some of the blocks in the block diagrams may represent a module, segment, or portion of program code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As will be appreciated by one skilled in the art, the disclosed subject matter may be embodied as a system, method or computer program product. Accordingly, the disclosed subject matter may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product embodied in any tangible medium of expression having computer-usable program code embodied in the medium.

Any combination of one or more computer usable or computer readable medium(s) may be utilized. The computer-usable or computer-readable medium may be, for example but not limited to, any non-transitory computer-readable medium, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CDROM), an optical storage device, a transmission media such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, RF, and the like.

Computer program code for carrying out operations of the present disclosure may be written in any combination of one or more programming languages, including an object oriented programming language such as Java, Smalltalk, C++ or the like and conventional procedural programming languages, such as the "C" programming language or similar programming languages. The program code may execute entirely on a first computer, partly on the first computer, as a stand-alone software package, partly on the first computer and partly on a second computer or entirely on the second computer or server. In the latter scenario, the second computer may be connected to the first computer through any type of network, including a local area network (LAN) or a wide area network (WAN), or the connection may be made to an external computer (for example, through the Internet using an Internet Service Provider).

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

What is claimed is:

1. A computer-implemented method performed by a computerized device, comprising:
   a. receiving a signal;
   b. determining an initial segment of the signal;
   c. inputting the initial segment into an element extraction engine to obtain a first element sequence;
   d. determining at least one second segment of the signal, the at least one second segment at least partially overlapping with the initial segment;
   e. inputting the at least one second segment into the element extraction engine to obtain at least one second element sequence; and
   f. searching for an element subsequence common to at least a predetermined number of sequences of the first element sequence and the at least one second element sequence.

2. The computer-implemented method of claim 1, further comprising outputting the element subsequence, subject to finding the element subsequence.

3. The computer-implemented method of claim 1, further comprising repeating steps (d), (e) and (f).

4. The computer-implemented method of claim 1, further comprising repeating steps (d), (e) and (f) subject to not finding the element subsequence.

5. The computer-implemented method of Claim 1, further comprising determining whether a stopping criterion has been met, and repeating steps (d), (e) and (f) only if the stopping criteria has not been met.

6. The computer-implemented method of claim 5, wherein the stopping criteria is selected from the group consisting of: a predetermined number of segments has been selected and the initial segment is fully covered by the at least one second segment.

7. The computer-implemented method of claim 1, wherein the initial segment is determined using a method selected from the group consisting of: energy-based; autocorrelation; zero crossing; and arbitrary determination.

8. The computer-implemented method of claim 1, wherein the element extraction engine is selected from the group consisting of: a Gaussian mixture model, an artificial neural network, a support vector machine, and a hidden Markov model.

9. The computer-implemented method of claim 1, wherein the signal is selected from the group consisting of: an audio signal, a video signal, a motion signal, a seismic signal, ECG signal, and a bio-medical signal.

10. The computer-implemented method of claim 1, wherein the element is a phoneme.

11. An apparatus having a processing unit and a storage device, the apparatus comprising:
- a signal receiving component for receiving a signal;
- an initial segmentation component for determining an initial segment of the signal;
- an additional segment determination component for determining at least one second segment of the signal, the at least one second segment at least partially overlapping with the initial segment;
- an element extraction engine for receiving the initial segment and the at least one second segment, and providing a first element sequence and at least one second element sequence; and
- an element sequence matching component for searching for a element subsequence common to at least a predetermined number of sequences of the first element sequence and the at least one second element sequence.

12. The apparatus of claim 11, wherein the element extraction engine is selected from the group consisting of: a Gaussian mixture model, an artificial neural network, a support vector machine, and a hidden Markov model.

13. The apparatus of claim 11, wherein the signal is selected from the group consisting of: an audio signal, a video signal, a motion signal, a seismic signal, ECG signal, and a bio-medical signal.

14. The apparatus of claim 11, wherein the element is a phoneme.

15. The apparatus of claim 11, further comprising a data and control flow management component.

16. A computer program product comprising:
- a non-transitory computer readable medium;
- a first program instruction for receiving a signal;
- a second program instruction for determining an initial segment of the signal;
- a third program instruction for inputting the initial segment into an element extraction engine to obtain a first element sequence;
- a fourth program instruction for determining at least one second segment of the signal, the at least one second segment at least partially overlapping with the initial segment;
- a fifth program instruction for inputting the at least one second segment into the element extraction engine to obtain at least one second element sequence; and
- a sixth program instruction for searching for an element subsequence common to at least a predetermined number of sequences of the first element sequence and the at least one second element sequences,
- wherein said first, second, third, fourth, fifth and sixth program instructions are stored on said non-transitory computer readable medium.

* * * * *